US012784897B2

(12) United States Patent
Yerebakan et al.

(10) Patent No.: US 12,784,897 B2
(45) Date of Patent: Nov. 3, 2026

(54) DETERMINING A LOCATION AT WHICH A GIVEN FEATURE IS REPRESENTED IN MEDICAL IMAGING DATA

(71) Applicant: Siemens Healthineers AG, Forchheim (DE)

(72) Inventors: Halid Yerebakan, Carmel, IN (US); Yoshihisa Shinagawa, Downingtown, PA (US); Kritika Iyer, Conshohocken, PA (US); Gerardo Hermosillo Valadez, West Chester, PA (US)

(73) Assignee: Siemens Healthineers AG, Forchheim (DE)

( * ) Notice: Subject to any disclaimer, the term of this patent is extended or adjusted under 35 U.S.C. 154(b) by 211 days.

(21) Appl. No.: 18/901,233

(22) Filed: Sep. 30, 2024

(65) Prior Publication Data

US 2025/0191735 A1 Jun. 12, 2025

(30) Foreign Application Priority Data

Dec. 11, 2023 (EP) .................................... 23215512

(51) Int. Cl.

*G16H 30/40* (2018.01)
*G06T 7/33* (2017.01)
*G06T 7/73* (2017.01)

(52) U.S. Cl.

CPC ............. *G16H 30/40* (2018.01); *G06T 7/337* (2017.01); *G06T 7/74* (2017.01); *G06T 2207/20081* (2013.01); *G06T 2207/30004* (2013.01)

(58) Field of Classification Search

CPC ........... G16H 30/40; G06T 7/337; G06T 7/74; G06T 2207/20081; G06T 2207/30004;

(Continued)

(56) References Cited

U.S. PATENT DOCUMENTS

2007/0280530 A1* 12/2007 Fung ..................... G06T 7/0012
382/159
2021/0035286 A1* 2/2021 Yoo ...................... A61B 5/0002

(Continued)

FOREIGN PATENT DOCUMENTS

WO 2023076147 A1 5/2023

OTHER PUBLICATIONS

EP search report in EP application No. 23215512.7, dated Apr. 17, 2024, 5 pages.

(Continued)

*Primary Examiner* — Amit Chatly

(57) ABSTRACT

A computer implemented method and apparatus for determining a location at which a given feature is represented in target medical imaging data is disclosed. The method includes determining, by inputting an initial descriptor for an initial location in the target medical imaging data to a trained machine learning model, an approximate location at which the given feature is represented. A plurality of candidate locations is determined based on the approximate location, and candidate descriptors for each of the plurality of candidate locations are obtained. A candidate location is selected from among the plurality of candidate locations based on similarity metrics between the candidate descriptors and a reference descriptor for a reference location in reference medical imaging data.

20 Claims, 8 Drawing Sheets

(58) Field of Classification Search
CPC ... G06T 2207/20084; G06T 7/33; G06T 7/77; G06T 7/73; G06T 2207/10024; G06T 2207/10081; G06T 2207/10088; G06T 2207/10116; G06T 2207/20101; G06T 2207/30061; G06T 7/0014; G06V 10/761; G06V 2201/03
See application file for complete search history.

(56) References Cited

U.S. PATENT DOCUMENTS

| | | | | |
|---|---|---|---|---|
| 2023/0005136 | A1 | 1/2023 | Yerebakan et al. | |
| 2023/0054641 | A1* | 2/2023 | Yang | G06T 7/74 |
| 2025/0104221 | A1* | 3/2025 | Shanbhag | G06T 5/40 |

OTHER PUBLICATIONS

Ghesu, Florin-Cristian, et al. "Multi-scale deep reinforcement learning for real-time 3D-landmark detection in CT scans." IEEE transactions on pattern analysis and machine intelligence 41.1 (2017): 176-189.

* cited by examiner

DETERMINING A LOCATION AT WHICH A GIVEN FEATURE IS REPRESENTED IN MEDICAL IMAGING DATA

CROSS-REFERENCE TO RELATED APPLICATION

This application claims the benefit of priority from European Patent Application No. 23215512.7, filed on Dec. 11, 2023, the contents of which are incorporated by reference.

TECHNICAL FIELD

The present framework relates to a method and apparatus for determining a location at which a given feature is represented in medical imaging data.

BACKGROUND

In medical imaging, it is often important to determine where a certain feature, such as a medical landmark (e.g. the tracheal carina), is represented in a medical image. Landmarks can be used to register different images into one coordinate system. For example, when comparing two images of a patient taken at different times, position and zoom of the images may be different. By registering them into one coordinate system, the images can be compared to evaluate the progress of a disease. Landmarks also have other uses, such as planning radiotherapy, and determining geometrical features (e.g. distances) in a human body.

One method for finding landmarks involves comparing a descriptor of the landmark in a reference medical image with candidate descriptors for candidate locations in the target medical image, and identifying the candidate location whose descriptor is the most similar to the reference descriptor. However, this requires testing candidate locations across the entire target medical image. Furthermore, the method may identify a candidate location as representing the landmark even if the landmark is not actually represented in the target medical image. As such, this method can be susceptible to returning 'false positive' indications of the location of a particular landmark in a target medical image, which is undesirable.

It is desirable to provide a reliable and efficient method for determining the location of a feature in medical imaging data.

SUMMARY

According to one aspect, there is a provided a computer-implemented method of determining a location at which a given feature is represented in target medical imaging data, the medical imaging data comprising an array of elements having respective values and representing respective locations. The method may include obtaining an initial descriptor for an initial location in the target medical imaging data, the initial descriptor being representative of values of elements of the target medical imaging data located relative to the initial location according to a first predefined pattern. An approximate location in the target medical imaging data at which the given feature is represented is determined based on an input of data representative of the initial descriptor to a trained machine learning model. A plurality of candidate locations in the target medical imaging data is further determined based on the approximate location. Candidate descriptors for each of the plurality of candidate locations are obtained, each candidate descriptor being representative of values of elements of the target medical imaging data located relative to the candidate location according to a second predefined pattern. A reference descriptor for a reference location in reference medical imaging data is obtained, the reference medical imaging data comprising one or more sets of reference medical imaging data, the reference location being, for each of the one or more sets of reference medical imaging data, a location in the set of reference medical imaging data at which the given feature is represented, the reference descriptor being representative of, for each of the one or more sets of reference medical imaging data, values of elements of the set of reference medical imaging data located relative to the reference location according to the second predefined pattern. For each of the plurality of candidate locations, the reference descriptor and the candidate descriptor for the candidate location are compared to obtain a similarity metric. A candidate location is selected from among the plurality of candidate locations based on the calculated similarity metrics. The location at which the given feature is represented in the target medical imaging data is determined based on the selected candidate location.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1:
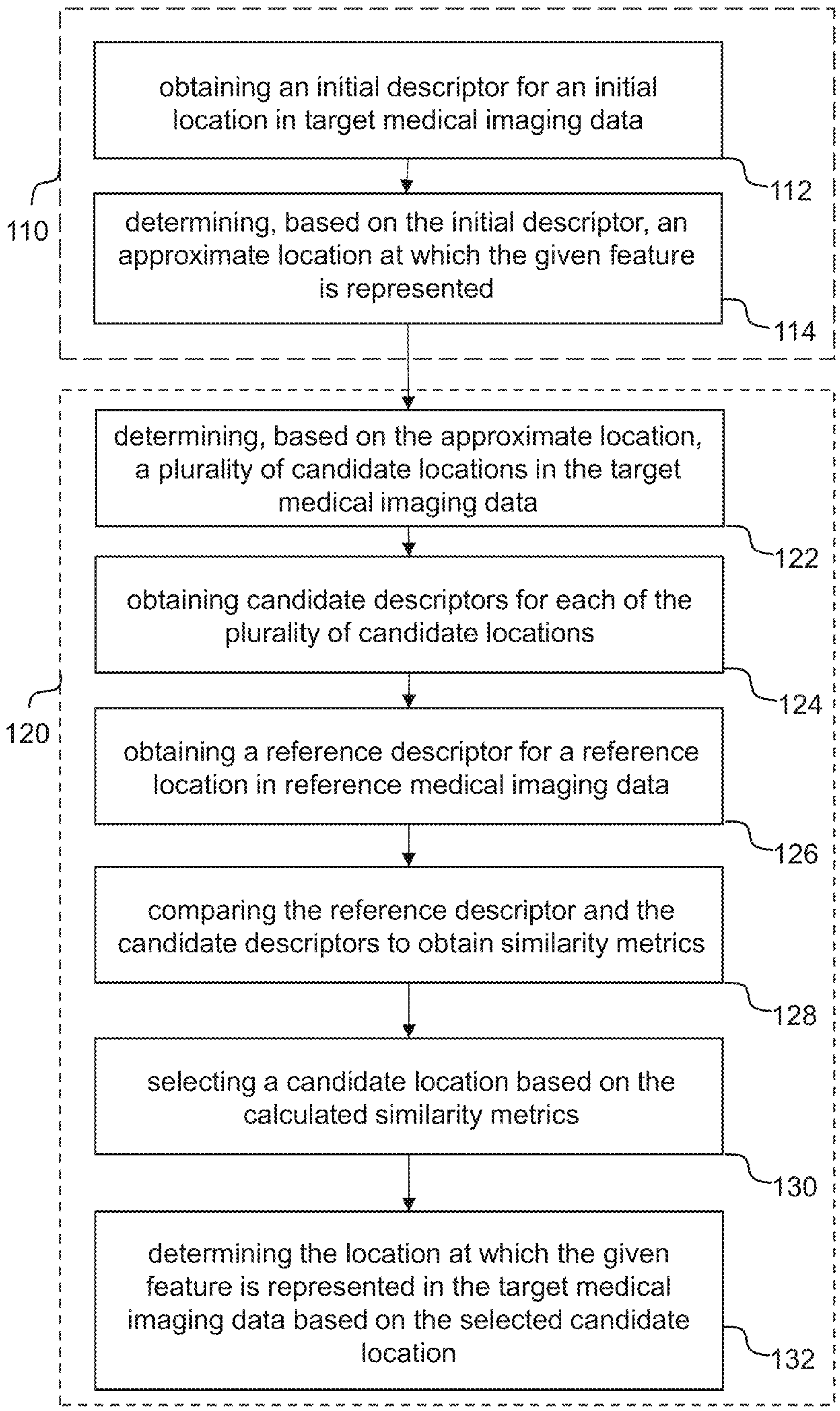
FIG. 1 is a flow diagram illustrating schematically a method for determining a location at which a given feature is represented in target medical imaging data.

According to a first aspect, there is a provided a computer implemented method of determining a location at which a given feature is represented in target medical imaging data, the medical imaging data comprising an array of elements having respective values and representing respective locations, the method comprising: obtaining an initial descriptor for an initial location in the target medical imaging data, the initial descriptor being representative of values of elements of the target medical imaging data located relative to the initial location according to a first predefined pattern; determining, based on an input of data representative of the initial descriptor to a trained machine learning model, an approximate location in the target medical imaging data at which the given feature is represented; determining, based on the approximate location, a plurality of candidate locations in the target medical imaging data; obtaining candidate descriptors for each of the plurality of candidate locations, each candidate descriptor being representative of values of elements of the target medical imaging data located relative to the candidate location according to a second predefined pattern; obtaining a reference descriptor for a reference location in reference medical imaging data, the reference medical imaging data comprising one or more sets of reference medical imaging data, the reference location being, for each of the one or more sets of reference medical imaging data, a location in the set of reference medical imaging data at which the given feature is represented, the reference descriptor being representative of, for each of the one or more sets of reference medical imaging data, values of elements of the set of reference medical imaging data located relative to the reference location according to the second predefined pattern; for each of the plurality of candidate locations, comparing the reference descriptor and the candidate descriptor for the candidate location to obtain a similarity metric; selecting a candidate location from among the plurality of candidate locations based on the calculated similarity metrics; and determining the location at which the given feature is represented in the target medical imaging data based on the selected candidate location.

Optionally, the method comprises: determining, based on the determined location at which the given feature is represented in the target medical imaging data, a plurality of further candidate locations in the target medical imaging data, wherein a distance between the further candidate locations is less than a distance between the candidate locations; obtaining further candidate descriptors for each of the plurality of further candidate locations, each further candidate descriptor being representative of values of elements of the target medical imaging data located relative to the further candidate location according to the second predefined pattern; for each of the plurality of further candidate locations, comparing the reference descriptor and the further candidate descriptor for the candidate location to obtain a further similarity metric; selecting a further candidate location from among the plurality of further candidate locations based on the further similarity metrics; and determining a refined location at which the given feature is represented in the target medical imaging data based on the selected further candidate location.

Optionally, the method comprises performing an image registration process using the location at which the given feature is represented in the target medical imaging data.

Optionally, the method further comprises using the computer implemented method of the first aspect to determine a location at which a further feature is represented in the target medical imaging data, wherein performing the registration process comprises performing the registration process using the location at which the further feature is represented in the target medical imaging data.

Optionally, determining the location at which the given feature is represented comprises determining, as the location at which the given feature is represented in the target medical imaging data, the selected candidate location.

Optionally, the one or more sets of reference medical imaging data comprises a plurality of sets of reference medical imaging data, and the reference descriptor is an averaged reference descriptor obtained from the plurality of sets of reference medical imaging data.

Optionally, the averaged reference descriptor is an average of a plurality of reference descriptors, each of the plurality of reference descriptors being for the reference location in a respective one of the plurality of sets of reference medical imaging data, and being representative of values of elements of the respective set of reference medical imaging data located relative to the reference location according to the second predefined pattern.

Optionally, determining the approximate location comprises: generating, based on an input of data representative of the initial descriptor to the trained machine learning model, an initial set of coordinates representing an initial body location in a template body, the initial body location in the template body corresponding to a body location, in a body at least a portion of which is represented by the target medical imaging data, represented at the initial location in the target medical imaging data; and based on the initial set of coordinates, a set of feature coordinates representing a location of the given feature in the template body, and the initial location, determining the approximate location.

Optionally, determining the approximate location comprises calculating a vector between the initial set of coordinates and the set of feature coordinates, and calculating the approximate location based on the initial location and the vector.

Optionally, calculating the approximate location comprises adding the vector to a vector representation of the initial location.

Optionally, the trained machine learning model has been trained to generate, based on an input of data representative of a given descriptor, a set of coordinates representing a body location in the template body, the given descriptor being representative of values of elements of given medical imaging data located relative to a given location in the given medical imaging data according to a first predefined pattern, the body location in the template body corresponding to a body location, in a body at least a portion of which is represented by the given medical imaging data, represented at the given location in the given medical imaging data.

Optionally, the method comprises a refining process to refine the approximate location, the refining process comprising: determining, based on the initial set of coordinates and the set of feature coordinates, a direction; determining, based on the initial location and the direction, a further initial location in the target medical imaging data; obtaining a further descriptor for the further initial location, the further descriptor being representative of values of elements of the target medical imaging data located relative to the further initial location according to the first predefined pattern; generating, based on the input of the data representative of the further descriptor to the trained machine learning model, a further initial set of coordinates representing a further initial body location in the template body, the further initial body location in the template body corresponding to a body location, in the body at least a portion of which is represented by the given medical imaging data, represented at the further initial location in the target medical imaging data; and based on the further initial set of coordinates, the set of feature coordinates representing the location of the given feature in the template body, and the further initial location, determining the approximate location.

Optionally, determining the direction comprises determining, as the direction, a direction of a vector between the initial set of coordinates and the set of feature coordinates.

Optionally, determining the further initial location comprises adding the vector between the initial set of coordinates and the set of features coordinates, to a vector representation of the initial location.

Optionally, the trained machine learning model has been trained by a training method comprising: providing a machine learning model configured to generate, based on an input of data representative of a given descriptor, a set of coordinates representing a body location in the template body, the given descriptor being representative of values of elements of given medical imaging data located relative to a given location in the given medical imaging data according to the first predefined pattern; providing training data comprising a plurality of training descriptors, each training descriptor being representative of values of elements of a given set of medical imaging data located relative to a given location in the given set of medical imaging data according to the first predefined pattern, the training data further comprising, for each training descriptor, a ground truth set of coordinates associated with a respective body location in the template body; and training the machine learning model based on the training data so as to minimize a loss function between sets of coordinates generated by the machine learning model based on the training descriptors and the corresponding ground truth sets of coordinates.

Optionally, providing the training data comprises obtaining one of the plurality of training descriptors by: obtaining a template descriptor for a reference location in template medical imaging data, the reference location in the template medical imaging data being a location in the template medical imaging data at which the respective body location is represented, the template descriptor being representative of values of elements of the template medical imaging data located relative to the reference location according to the second predefined pattern; obtaining candidate descriptors for each of a plurality of candidate locations in the given set of medical imaging data, each candidate descriptor being representative of values of elements of the given set of medical imaging data located relative to the candidate location according to the second predefined pattern; for each of the plurality of candidate locations in the given set of medical imaging data, comparing the template descriptor and the candidate descriptor for the candidate location to obtain a template similarity metric; and determining the training descriptor based on the candidate descriptors and the calculated template similarity metrics.

According to a second aspect, there is provided an apparatus configured to perform the method of the first aspect.

According to a third aspect, there is provided a computer program which when executed by a computer causes the computer to perform the method of the first aspect.

Referring to FIG. 1, there is illustrated computer implemented method of determining a location at which a given feature 226 is represented in target medical imaging data 330.

Representations of example medical imaging data with which the method may be used are illustrated in FIGS. 2, 3, and 5 to 10. Medical imaging data may be that captured from performing medical imaging on a patient, for example Computed Tomography (CT), Magnetic Resonance Imaging (MRI), X-ray, or other imaging techniques.

Figure 5A:
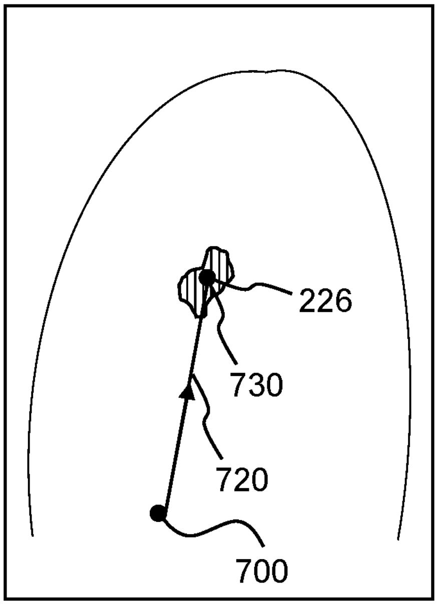
FIG. 5*a* is a diagram illustrating schematically reference medical imaging data according to another example.
Figure 5B:
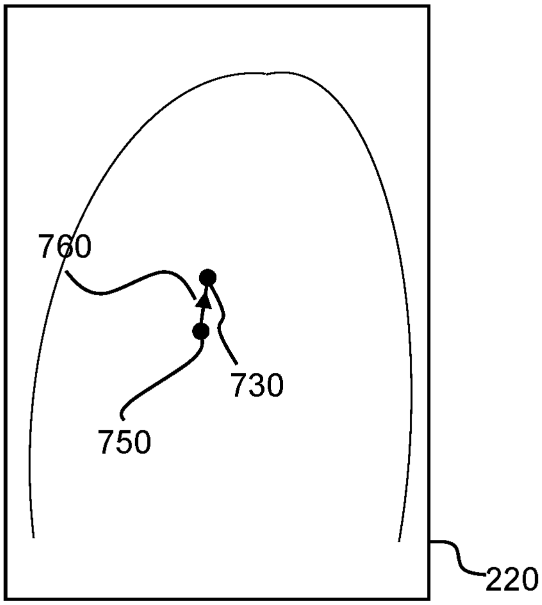
FIG. 5*b* is a diagram illustrating schematically reference medical imaging data according to another example.
Figure 6A:
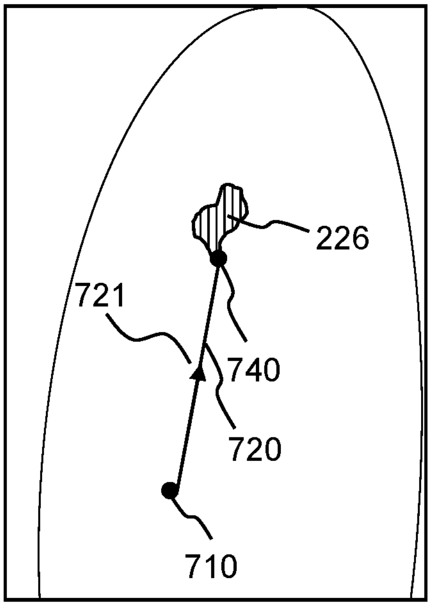
FIG. 6*a* is a diagram illustrating schematically target medical imaging data according to another example.
Figure 6B:
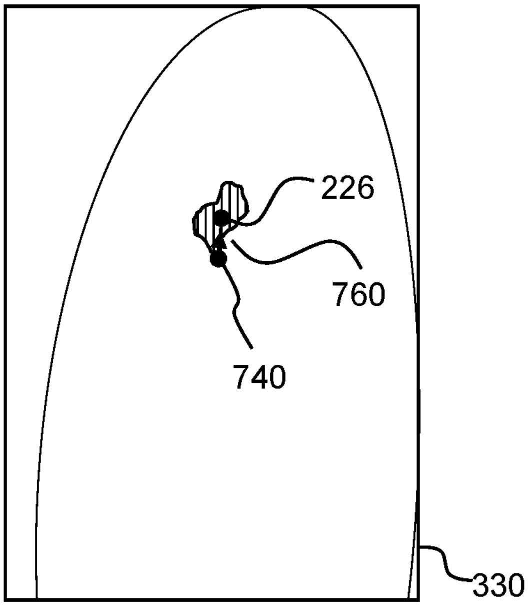
FIG. 6*b* is a diagram illustrating schematically target medical imaging data according to another example.
Figure 7:
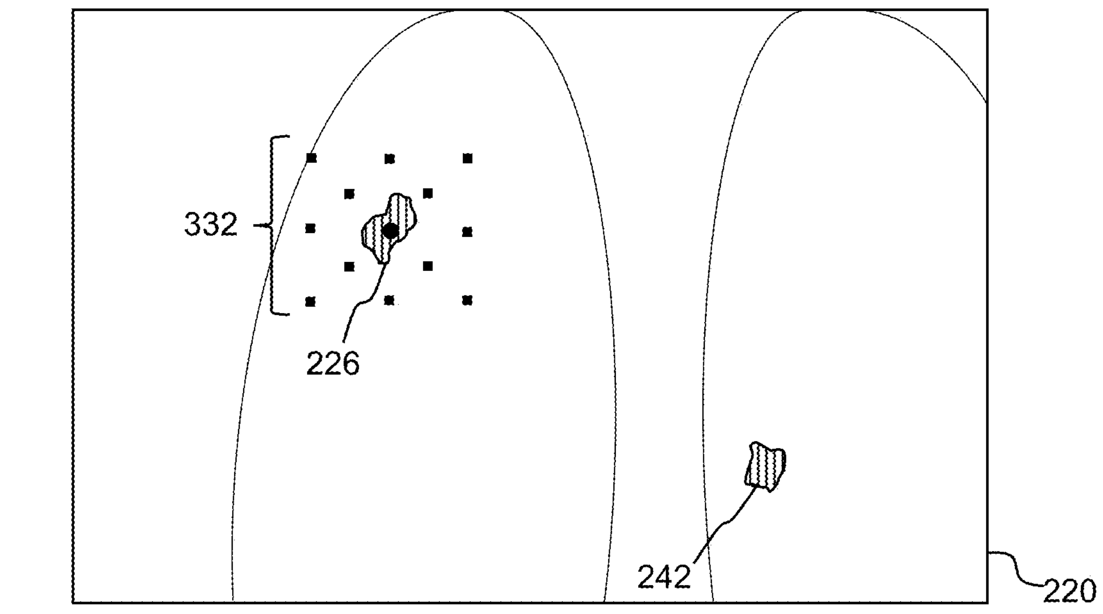
FIG. 7 is a diagram illustrating schematically reference medical imaging data according to another example.

FIGS. 5*a*, 5*b* and 7 each illustrate a representation of reference medical imaging data 220. FIGS. 2, 3, 6*a*, 6*b*, and 8 to 10 each illustrate a representation of target medical imaging data 330. In each case, the medical imaging data comprises an array of elements each having a value. For example, the medical imaging data may comprise a 2-Dimensional array of pixels, each pixel having at least one value. As another example, the medical imaging data may comprise a 3-Dimensional array of voxels, each voxel having at least one value. The at least one value may correspond to or otherwise be representative of an output signal of the medical imaging technique used to generate the medical imaging data. For example, for X-ray imaging, the value of an element (e.g. pixel) may correspond to or represent a degree to which X-rays have been detected at the particular part of the imaging plane corresponding to the element. As another example, for Magnetic Resonance Imaging, the value of an element (e.g. voxel) may correspond to or represent a rate at which excited nuclei, in a region corresponding to the element, return to an equilibrium state. In some examples, each element may only have one value. However, in other examples, each element may have or otherwise be associated with multiple values. For example, the multiple values of a given element may represent the values of respective multiple signal channels. For example, each signal channel may represent a different medical imaging signal or property of the imaging subject. In some examples, the at least one value may comprise an element (e.g. pixel or voxel) intensity value. For example, an output signal from the medical imaging may be mapped onto a pixel or voxel intensity value, for example a value within a defined range of intensity values. For example, for a greyscale image, the intensity value may correspond to a value in the range 0 to 255, where 0 represents a 'black' pixel and 255 represents a 'white' pixel, for example. As another example, for example as in the case of USHORT medical image data, the intensity value may correspond to a value in the range 0 to 65536. As another example, in a color image (e.g. where different colors represent different properties of the imaging subject) each pixel/voxel may have three intensity values, e.g. one each for Red, Green, and Blue channels. It will be appreciated that other values may be used. In any case, the medical imaging data may be rendered into an image, for example as schematically illustrated in FIGS. 2, 3, and 5 to 10.

In the illustrated examples, the reference medical imaging data 220 and the target medical imaging data 330 are data captured by performing medical imaging, using the same modality, on the same region of different patients. However, in some examples, the modality (i.e. the medical imaging method by which the data was captured) and/or the protocol (i.e. the specific parameters by which a given method of medical imaging was performed) of the medical imaging may be different between the reference medical imaging data 220 and the target medical imaging data 330. Furthermore, in some examples, the reference medical imaging data 220 comprises a single panoramic "atlas" medical image of an entire patient's body.

As can be seen, certain features 226, 242 are represented in both the first medical imaging data 220 and the second medical imaging data 330. The present framework is described largely using medical landmarks (e.g. the tracheal carina) as example features. It will be appreciated, however, that in examples the given feature may be any feature, e.g. any particular part of the imaging subject (e.g. including internal cavities and the like), represented in the medical imaging data.

Referring again to FIG. 1, in broad overview, the method comprises:

in step 112, obtaining an initial descriptor for an initial location 710 in the target medical imaging data 330, the initial descriptor being representative of values of elements of the target medical imaging data 330 located relative to the initial location 710 according to a first predefined pattern;

in step 114, determining, based on an input of data representative of the initial descriptor to a trained machine learning model 715, an approximate location in the target medical imaging data 330 at which the given feature 226 is represented;

in step 122, determining, based on the approximate location, a plurality of candidate locations 442 in the target medical imaging data 330;

in step 124, obtaining candidate descriptors for each of the plurality of candidate locations 442, each candidate descriptor being representative of values of elements of the target medical imaging data 330 located relative to the candidate location according to a second predefined pattern 440;

in step 126, obtaining a reference descriptor for a reference location in reference medical imaging data 220, the reference medical imaging data 220 comprising one or more sets of reference medical imaging data 220, the reference location being, for each of the one or more sets of reference medical imaging data 220, a location in the set of reference medical imaging data 220 at which the given feature 226 is represented, the reference descriptor being representative of, for each of the one or more sets of reference medical imaging data 220, values of elements of the set of reference medical imaging data 220 located relative to the reference location according to the second predefined pattern 440;

in step 128, for each of the plurality of candidate locations 442, comparing the reference descriptor and the candidate descriptor for the candidate location to obtain a similarity metric;

in step 130, selecting a candidate location from among the plurality of candidate locations 442 based on the calculated similarity metrics; and in step 132, determining the location at which the given feature 226 is represented in the target medical imaging data 330 based on the selected candidate location.

Accordingly, a technique for determining the location at which a given feature 226 is represented in target medical imaging data 330 is provided for. This may, for example, reduce the burden for a physician in finding the location at which the given feature 226 is represented in the target medical imaging data 330.

The method consists of a two-stage process. In the first stage, hereinafter referred to as the BodyGPS method 110, an approximate location at which the given feature 226 is represented is determined using a trained machine learning model 715. The BodyGPS method 110 includes steps 112 and 114. In the second stage, hereinafter referred to as the point matching method 120, the approximate location is used to determine the location at which the given feature 226 is represented. The point matching method 120 includes steps 122 to 132.

As described below, using the BodyGPS method 110 to firstly estimate the approximate location, and subsequently using the point matching method 120 to refine the approximate location, reduces the risk of a false positive finding of the location of the given feature 226 when the given feature 226 is not represented in the target medical imaging data 330, as compared with using the point matching method 120 alone. In addition, the method is more computationally efficient than using the point matching method 120 alone.

Furthermore, while the BodyGPS method alone can be used to estimate the approximate location, the additional use of the point matching method 120 can improve the accuracy of the determination of the location. This is because the accuracy with which the machine learning model of the BodyGPS method can output body coordinates is limited, as the granularity of locations on the basis of which the machine learning model has been trained is limited. On the other hand, the point matching method involves directly comparing the target medical imaging data 330 with reference medical imaging data 220, which can be done with arbitrary granularity, for example down to an individual pixel level.

As mentioned above, the method comprises, in step 112, obtaining an initial descriptor for an initial location 710 in the target medical imaging data 330. The initial descriptor is representative of values of elements of the target medical imaging data 330 located relative to the initial location 710 according to a first predefined pattern.

The initial location 710 can be chosen arbitrarily. In some examples, the center point of the target medical imaging data 330 is selected as the initial location.

Alternatively, a medical professional viewing the target medical imaging data 330 may select the initial location 710 by reviewing the target medical imaging data 330, identifying the given feature 226, and selecting, as the initial location 710, a location near to the location at which the given feature 226 is represented.

In some examples, the initial descriptor may be output from a descriptor model applied to the target medical imaging data 330 for the initial location. The descriptor model may be configured to calculate a descriptor for a given location based on the values of elements located relative to the given location according to the first predefined pattern.

A descriptor for a given location may be a vector comprising a plurality of entries, each entry being representative of the value (e.g. an intensity value) of an element (e.g. a pixel or voxel), the elements being located relative to the given location according to a predefined pattern. The first predefined pattern may be, for example, a e grid-like pattern, such as the grid-like pattern 332 shown in FIG. 2. In some examples, the descriptor may be determined using many such values of elements, for example 100 elements, and accordingly the descriptor may be a vector having many entries (e.g. 100 entries). For example, briefly referring to FIG. 3, there is presented, for illustrative purposes, a medical imaging data set 660 to which a complex grid containing a large number of points (shown as white dots) has been applied in order to determine a descriptor for a given location at the center of this grid. As can be seen, the density of locations in the predefined pattern decreases as the distance from the given location increases. A second predefined pattern 440 is used in the point matching method 120, and a first predefined pattern is used in the BodyGPS method 110. These predefined patterns may be the same pattern.

The descriptor may encode the spatial context of the given location at which a given feature 226 is represented, and hence in turn may provide a compact representation of the surroundings of a given feature 226.

It will be appreciated that, in some examples, descriptors other than the specific example described above may be used. For example, in some examples, each entry may be representative of the values of the elements located within a respective one or more of a plurality of predefined boxes (i.e. rectangular regions) located relative to the given location according to the first predefined pattern. It will be appreciated that, where the medical imaging data exists in three spatial dimensions, the term 'box' as used herein may refer to a cuboidal region or volume. In some examples, each entry of the descriptor may be representative of the values of the elements located within a respective one of a plurality of predefined boxes. For example, each entry of the descriptor may be an average of the values of the elements located within a respective one of a plurality of predefined boxes. That is, each entry may be the sum of the values of the elements located within a particular box, divided by the number of elements included in the box.

Alternatively, in some examples, Haar-like descriptors may be used, i.e. a descriptor where each entry represents a difference between the sums of element values within each of a plurality of boxes defined in the image data. In some examples, the descriptor may be a gradient descriptor, for example in which each entry represents one or more image gradients in a respective one of a plurality of regions of the medical image data. For example, an image gradient for a given region may be based on a change in the values (e.g. intensity values) between elements within the given region. In some examples, the descriptor may be such that each entry is the value of a respective one of a plurality of elements randomly distributed in the medical imaging data relative to the given location. In some examples, the descriptor for a given location may be such that each entry is the aggregate of the values of elements intersecting with a respective one of a plurality of randomly orientated rays, each ray originating from the given location. In each case, the descriptor for a given location is representative of values of elements of the medical imaging data located relative to the given location according to a first predefined pattern. Other descriptors may be used.

As mentioned above, the method comprises, in step 114, determining, based on an input of data representative of the initial descriptor to a trained machine learning model 715, an approximate location in the target medical imaging data 330 at which the given feature 226 is represented. The trained machine learning model 715 may have been trained to determine, based on an input of data representative of the initial descriptor, an approximate location in the target medical imaging data 330 at which the given feature 226 is represented.

Figure 2:
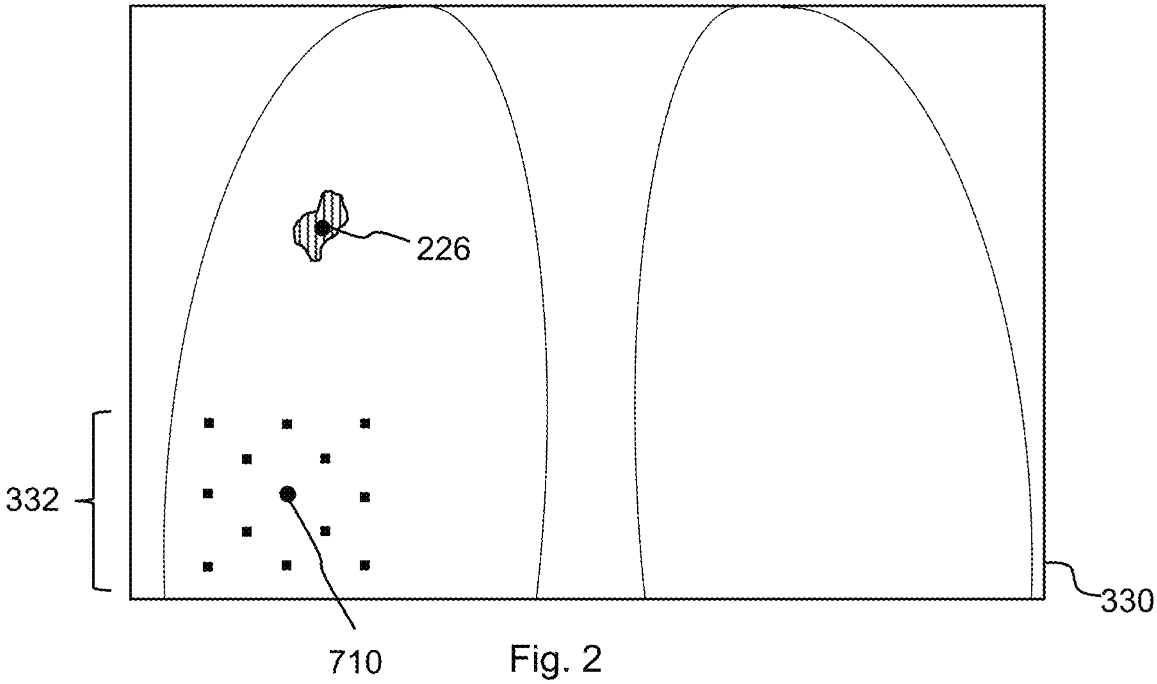
FIG. 2 is a diagram illustrating schematically target medical imaging data according to an example.
Figure 3:
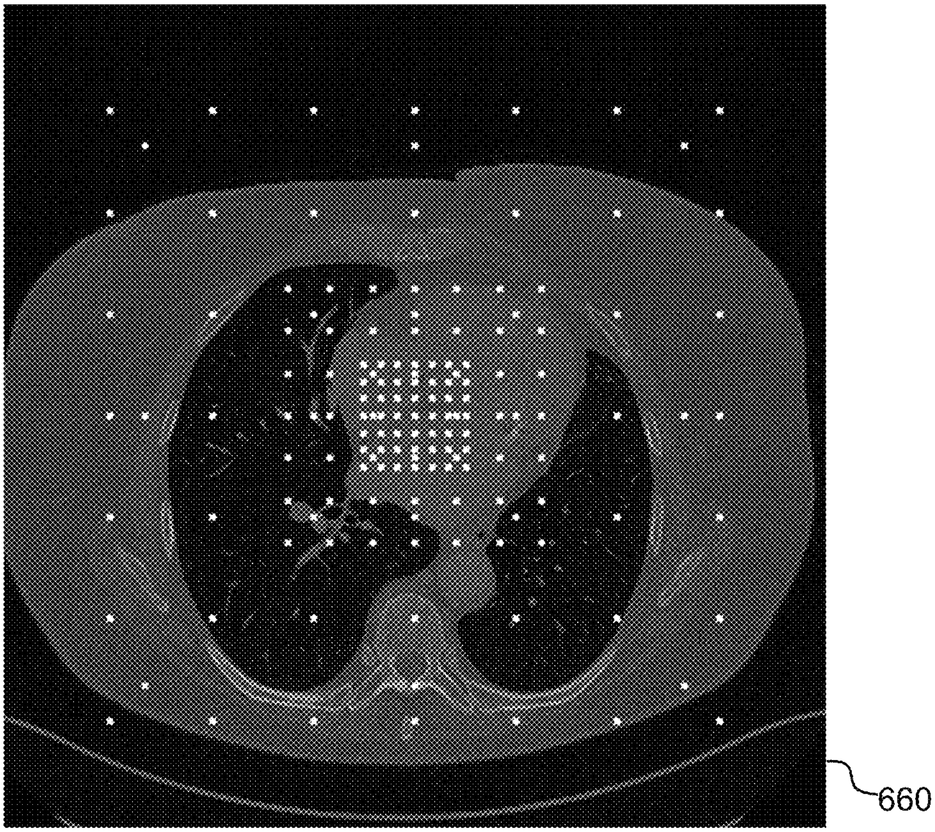
FIG. 3 is a diagram illustrating schematically target medical imaging data according to an example.

The given feature 226 may comprise a medical landmark. Example medical landmarks include the tracheal carina, the center of the right thumbnail, and the apex (highest point) of the upper lobe of the right lung. The given feature 226 illustrated in FIG. 2 is purely illustrative. It is a landmark that occurs in the upper lobe of the right lung.

Figure 4:
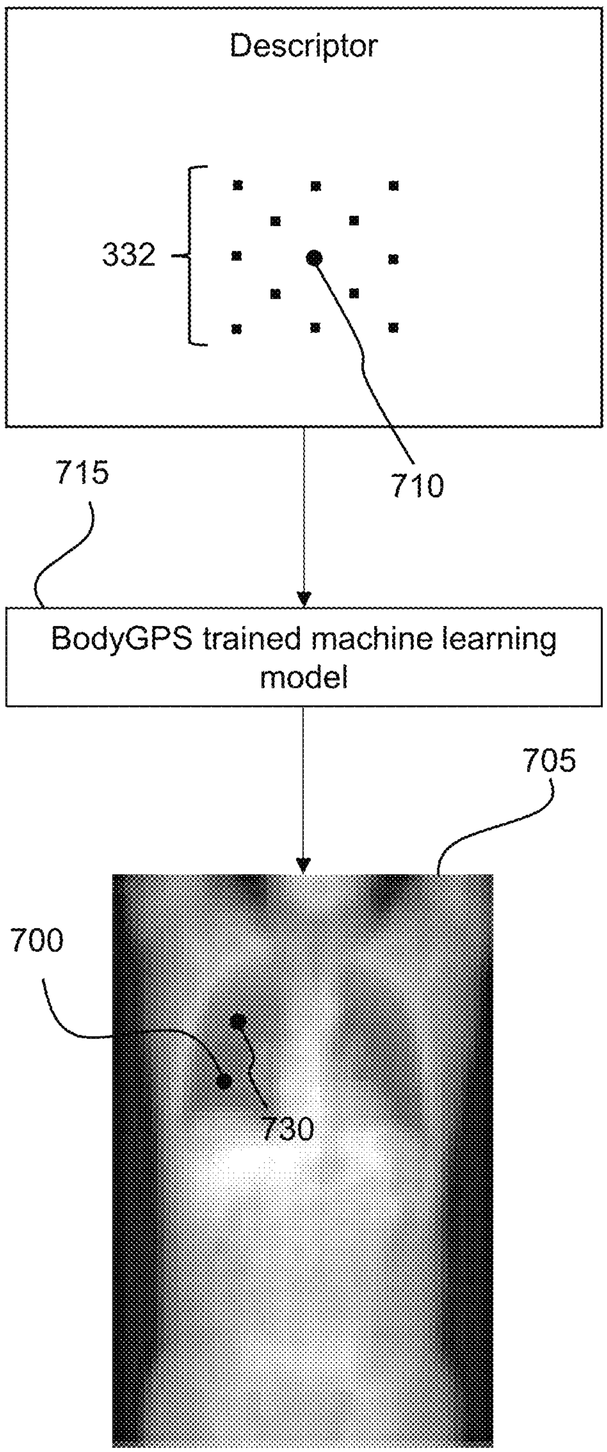
FIG. 4 is a diagram illustrating schematically a trained machine learning model according to an example.

Referring to FIG. 4, an example method performed by the trained machine learning model 715 is illustrated. In this example, determining the approximate location comprises generating, based on an input of data representative of the initial descriptor to the trained machine learning model 715, an initial set of coordinates 700 representing an initial body location in a template body 705. The template body 705 may, for example, be a human body that is depicted in reference medical imaging data 220. An example of the reference medical image data is depicted in FIG. 7. The reference medical imaging data 220 comprises one or more sets of reference medical imaging data 220. The reference medical imaging data 220 may consist of, for example, one set of reference medical imaging data 220, the set of reference medical imaging data 220 representing one study on one patient. The patient represented may be selected as an "average Joe" or "average Jane" patient; that is, a patient whose body metrics are similar to the average of the population. The reference medical imaging data 220 may be for a part of the patient, for example their lungs. Alternatively, the reference medical imaging data 220 may comprise a plurality of sets of medical imaging data depicting respective body portions of one patient. An image registration process may be performed on the sets of medical imaging data to form a single panoramic "atlas" medical image of the patient. The panoramic image may be a volumetric image.

The initial set of coordinates 700 can be thought of as a universal set of coordinates that indicates a location in the template body 705. For example, the origin of this coordinate system may be the tracheal carina. The positive z-axis of the coordinate system may be directed towards the head. The positive x-axis of the coordinate system may be directed towards the right arm. The positive y-axis of the coordinate system may be directed towards the sternum. However, this is purely exemplary, and spherical or cylindrical coordinates may be used in place of cartesian coordinates, the origin may be located in any body part, and the coordinate system may have any orientation.

In this example, the trained machine learning model 715 has been trained to generate, based on an input of data representative of a given descriptor, a set of coordinates representing a body location in the template body 705. Here, the given descriptor is representative of values of elements of given medical imaging data located relative to a given location in the given medical imaging data according to the first predefined pattern. The body location in the template body corresponds to a body location, in a body at least a portion of which is represented by the given medical imaging data, represented at the given location in the given medical imaging data.

In any case, the initial body location corresponds to a location in the imaged body represented by an initial element. For example, if the initial element (representing the initial location 710 for which the initial descriptor was obtained) represents a point in the right lung of the imaged body, then the initial set of coordinates 700 represents the same point in the right lung of the template body 705.

An example of the training of the machine learning model is described below.

The present framework uses the knowledge that different bodies depicted in different medical images have a similar arrangement of organs, landmarks, and other medical features. Therefore, the vector joining two locations, such as two landmarks in one body, is likely to be similar (in direction and/or magnitude) to the vector joining the same two locations in a different body. present framework The present framework exploits this knowledge to determine the approximate location at which the given feature 226 is represented, as will now be described with reference to FIGS. 5*a* to 6*b*.

FIG. 5*a* shows a simplified representation of the template body 705, on which a set of feature coordinates 730 representing a location of the given feature 226 in the template body 705, and the initial set of coordinates 700, have been indicated. FIG. 6*a* shows a portion of the target medical imaging data 330 with the initial location 710 and the approximate location 740 indicated.

In this example, determining the approximate location 740 at which the given feature 226 is represented comprises determining the approximate location 740 based on the initial set of coordinates 700, a set of feature coordinates 730 representing a location of the given feature 226 in the template body 705, and the initial location 710 (being the location described by the initial descriptor).

The set of feature coordinates 730 is, for example, a set of coordinates that represents the location of the given feature 226 in the right lung of the template body 705. In such a case, it is desired to determine the location, in the target medical imaging data 330, of this feature of the right lung (of the imaged body).

In this example, the given feature 226 is a feature which is selected by a user. The set of feature coordinates 730 may be obtained from a database (not shown), which stores sets of feature coordinates in association with respective features (e.g. medical landmarks) that are represented in the template body 705. The database can be used to extract the set of feature coordinates based on the selection of the given feature 226.

Alternatively, in some examples, the method comprises comparing the initial set of coordinates 700 with the sets of feature coordinates stored in the database, to identify the feature that is closest in the template body 705 to the initial set of coordinates 700. The set of feature coordinates associated with this closest feature may be selected as the set of feature coordinates 730 to be used.

In some examples, determining the approximate location comprises calculating a vector 720 between the initial set of coordinates 700 and the set of feature coordinates 730, and then calculating the approximate location based on the initial location 710 and the vector 720. The vector 720 between the initial set of coordinates 700 may be calculated by subtracting the initial set of coordinates 700 from the set of feature coordinates 730. The approximate location may be calculated by adding the vector 720 to a vector representation of the initial location 710 in the target medical imaging data 330. For example, if the initial set of coordinates 700 is (0.5, 0, −0.2), and the set of coordinates of the given feature 226 in the template body 705 is (0.4, 0, 0.7), then the vector 720 (−0.1, 0, 0.9) can be added to a vector representation of the initial location 710 in the target medical imaging data 330. The target medical imaging data 330 may comprise a grid of voxels arranged along three axes and in such a case the vector representation of the initial location 710 may be, for example, a vector representing the position of the voxel corresponding to the initial location 710, with respect to these axes.

In some cases, the determined approximate location may be a location outside of the range of the target medical imaging data 330. For example, where the target medical imaging data 330 depicts only the abdomen, and the feature to be found is a landmark on the foot, the determined approximate location might be a location which is not represented in the target medical imaging data 330. In such a case, the method may comprise determining that the approximate location is outside of an imaged portion of the imaged body, and outputting data indicating that the approximate location is outside of the imaged portion of the imaged body. For example, a processor 502 executing the method may output, to a display device (not shown), an indication that the approximate location is outside of the imaged portion of the imaged body, such as a message stating "The feature is not contained in this image."

As described herein, the point matching method when used alone can give rise to false positive indications of the location of the given feature 226. However, by using the BodyGPS method 110 prior to using the point matching method as per the example described herein, this risk of generating false positive indications of the location of the given feature 226 can be eliminated or reduced.

In some examples, the trained machine learning model 715 outputs directly the vector 720 between the initial set of coordinates 700 and the set of feature coordinates 730, rather than outputting the initial set of coordinates 700.

Since the arrangement of (i.e. the vector 720 separating) the set of feature coordinates 730 and the initial set of coordinates 700 in the template body 705 is similar to the arrangement of (i.e. the vector 720 separating) the location of the given feature 226 and the initial location 710 in the target medical imaging data 330, the approximate location determined by adding the vector 720 to the initial location 710 provides the approximate location 740 at which the given feature 226 is represented. Accordingly, in some examples, this may be taken as the approximate location at which the given feature 226 is represented in the target medical imaging data 330.

However, as can be seen in FIGS. 5*a* and 6*a*, the lungs in the template body 705 are smaller than the lungs in the imaged body. As a result, the magnitude of the vector 720 used is an underestimate, and the approximate location determined is not exactly where the given feature 226 is represented in the imaged body.

To mitigate against this, in some examples, the BodyGPS method 110 comprises performing a refining process to refine the approximate location, which is described with reference to FIGS. 5*b* and 6*b*. FIG. 6*b* shows the portion of the target medical imaging data 330 shown in FIG. 6*a*, illustrating a first iteration of the refining process. FIG. 5*b* shows the portion of the reference medical imaging data 220 shown in FIG. 5*a*, illustrating the first iteration of the refining process.

The refining process comprises determining, based on the initial set of coordinates 700 and the set of feature coordinates 730, a direction 721. This may comprise determining, as the direction 721, a direction of the vector 720 between the initial set of coordinates 700 and the set of feature coordinates 730. However, any direction that is towards the set of features coordinates 730 from the initial set of coordinates 700, may be used.

The refining process comprises determining, based on the initial location 710 and the direction 721, a further initial location 740 in the target medical imaging data 330. The further initial location 740 is located relative to the initial location 710 in the calculated direction 721. In some examples, including the example shown in FIG. 6*b*, determining the further initial location 740 comprises adding the vector 720 to the initial location 710; that is, the further initial location 740 is the same as the approximate location 740 calculated previously. However, in other examples, a vector having the calculated direction 721 but with a predetermined step size (e.g. ten voxels) may be used. That is, the further initial location 740 may be located away from the initial location 710 in the direction 721 of the vector 720 but by a fixed distance. This may provide for robust approximate location determination in examples in which the scale of the template body 705 is not matched to the scale of the target medical imaging data 330.

The refining process comprises obtaining a further descriptor for the further initial location 740. The further initial descriptor is representative of values of elements of the target medical imaging data 330 located relative to the further initial location 740 according to the first predefined pattern. The further initial descriptor may be calculated in a similar fashion to the initial descriptor.

The refining process comprises generating, based on the input of the data representative of the further descriptor to the trained machine learning model 715, a further initial set of coordinates 750 representing a further initial body location in the template body 705. Similarly to the initial body location, the further initial body location corresponds to a location in the imaged body (e.g. a location near the given feature 226 as shown in FIGS. 6*a* and 6*b*) represented at a further initial location 740 in the target medical imaging data 330.

The refining process also comprises determining the approximate location based on the further initial set of coordinates 750, the set of feature coordinates 730 representing the location of the given feature in the template body 705, and the further initial location 740. In a similar fashion to that described above, the further initial set of coordinates 750 and the set of feature coordinates 730 can be used to determine the refined approximate location. For example, the refining process may comprise determining a further vector 760, being a vector 760 between the further initial set of coordinates 750 and the set of feature coordinates 730. The further vector 760 may be added to a vector representation of the further initial location 740 to determine the refined approximate location.

Further iterations of the refining process may be performed. The refining process may cease after a fixed number of iterations have been performed. Alternatively, in some examples, the refining process may cease in response to determining that a criterion has been met. For example, at each iteration, the distance between the approximate location before the iteration and the refined approximate location after the iteration, may be compared with a criterion. The criterion may comprise a threshold, such as a predefined number of pixels or voxels. The method may comprise, in response to the comparison, determining the refined approximate location as the approximate location to use as input to the point matching method 120. For example, if the distance is lower than the threshold, the method may comprise determining the refined approximate location after this iteration as the approximate location to use as input to the point matching method 120. Alternatively, and in particular in examples in which a predetermined step size is used, a different criterion may be used. For example, the refined approximate location is used to perform a second iteration of the refining process to arrive at a further refined approximate location. The vector between the approximate location before the first iteration and the refined approximate location after the first iteration, may be compared with the vector between the refined approximate location and the further refined approximate location. If the angle between these two vectors is greater than a threshold, for example 90 degrees, the method may comprise determining the further refined approximate location as the approximate location to use as input to the point matching method 120. Ceasing the refining process when the criterion is met may improve the computational efficiency of the BodyGPS system while maintaining a degree of accuracy in the outputted approximate location.

In any case, the BodyGPS method 110 comprises determining the approximate location at which the given feature 226 is represented in the target medical imaging data 330. The approximate location is then used as an input to the point matching method 120.

The BodyGPS method 110 alone can provide an approximate location at which the given feature 226 (e.g. landmark) is represented in the medical image. Furthermore, the BodyGPS method 110 can avoid false positive determinations of the location of the given feature 226, as described above. However, even when performing the refining process described above, the trained machine learning model has limited precision in mapping a location to a body location in the template body. To mitigate against this, the present framework uses the determined approximate location as input to a point matching method 120 which involves directly comparing descriptors obtained from the target medical imaging data 330 with reference medical imaging data 220.

Figure 8:
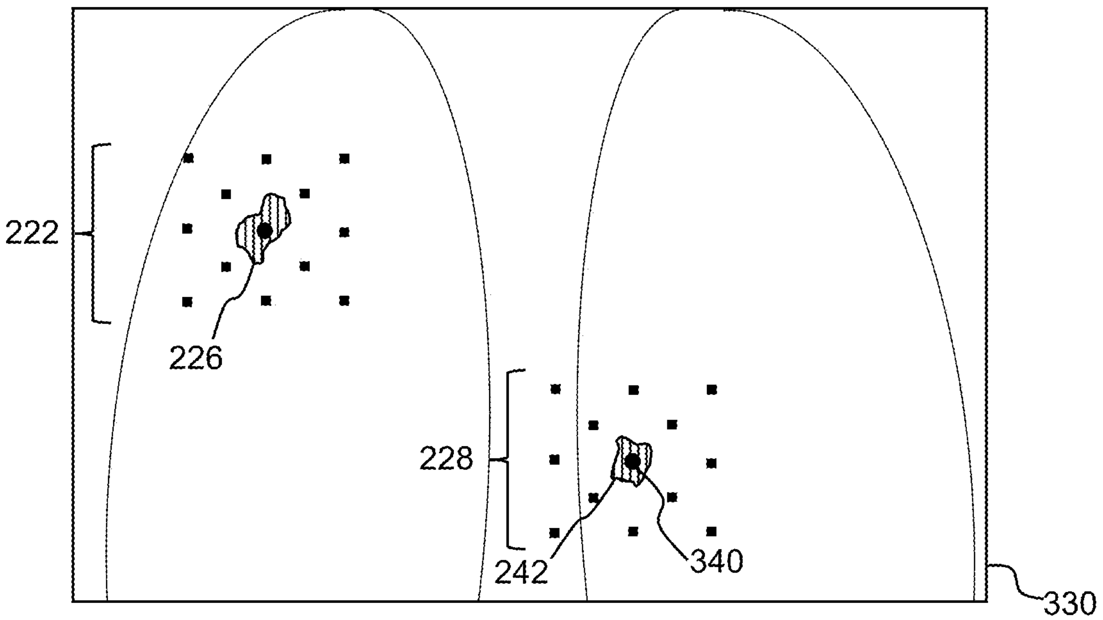
FIG. 8 is a diagram illustrating schematically target medical imaging data according to another example.
Figure 9:
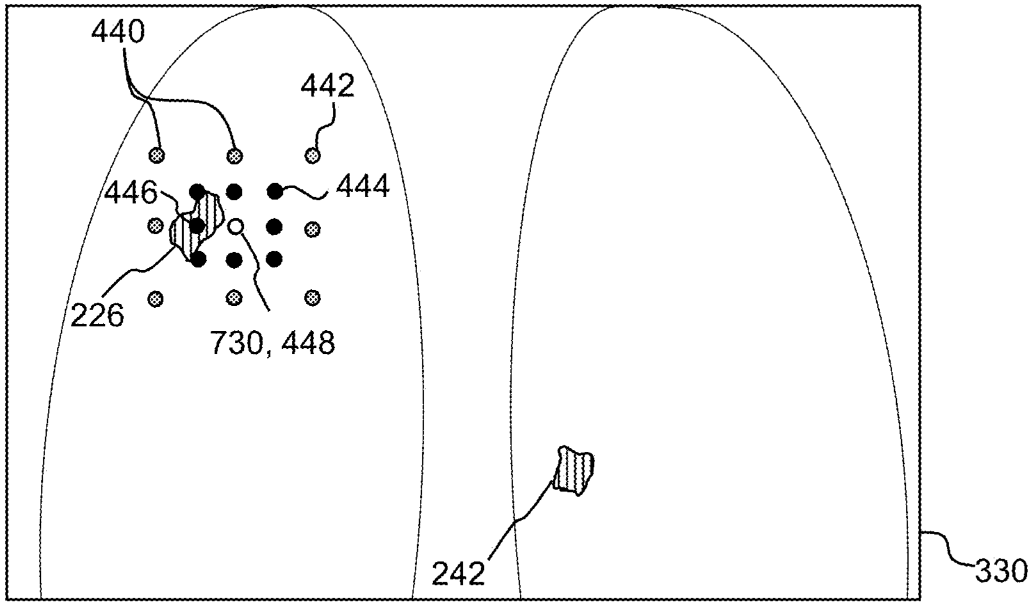
FIG. 9 is a diagram illustrating schematically target medical imaging data according to another example.

Now is described the point matching method 120 with reference to FIGS. 7 to 9.

As mentioned, the method comprises, at step 122, determining, based on the approximate location in the target medical imaging data 330 at which the given feature 226 is represented, a plurality of candidate locations in the target medical imaging data 330.

Locations having less than a predefined distance from the approximate location may be selected as the plurality of candidate locations 442. For example, where the scale of the target medical imaging data 330 is known, the plurality of candidate locations 442 may be selected to have a distance of, for example, less than 2 cm from the approximate location. Alternatively, the plurality of candidate locations 442 may be selected to have a distance of fewer than a predefined number of pixels or voxels from the approximate location. The plurality of candidate locations 442 may comprise a 3×3 square grid of candidate locations centered on the approximate location, as shown in FIG. 9.

As mentioned, in step 124, the method comprises obtaining candidate descriptors for each of the plurality of candidate locations 442.

Each candidate descriptor is representative of values of elements of the target medical imaging data 330 located relative to the candidate location according to a second predefined pattern 440. The same descriptor model that was applied to the target medical imaging data 330 to generate the initial descriptor for the initial location may be applied to the target medical imaging data 330 to generate the candidate descriptor for each of the plurality of candidate locations 442. For example, referring to FIGS. 7 and 8, the grids 222, 228 and the locations of the elements relative to each candidate location, 340 used to calculate the candidate descriptor for each of those candidate locations, 340 are the same as the grid 332 and the location of the elements relative to the initial location used to calculate the initial descriptor for the initial location.

As mentioned, the method comprises, at step 126, obtaining a reference descriptor for a reference location in reference medical imaging data 220.

The reference medical imaging data 220 may be the reference medical imaging data 220 that forms the template body 705 described above in the BodyGPS method. However, in some examples, it is different from the medical imaging data used in the BodyGPS method.

In this example, the reference location is a location in the set of reference medical imaging data 220 at which the given feature 226 is represented. The reference descriptor is representative of, for each of the one or more sets of reference medical imaging data 220, values of elements of the set of reference medical imaging data 220 located relative to the reference location according to the second predefined pattern 440. The same descriptor model that was applied to the target medical imaging data 330 to generate the initial descriptor for the initial location may be applied to the reference medical imaging data 220 to generate the reference descriptor for the reference location.

In some examples, the reference descriptor may be obtained from a database (not shown). For example, the descriptor for the reference location may have already been calculated (for example by applying the descriptor model), and stored in the database, for example in association with the given feature 226 and the reference location. For example, the database may store a plurality of reference descriptors each in association with the corresponding reference location in the medical imaging data on the basis of which the reference descriptor was determined, and with a corresponding feature represented by the reference location. Accordingly, in some examples, the method may comprise selecting the given feature 226 from among the plurality of features and extracting the reference descriptor associated with the given feature 226. The given feature 226 can be selected by a user and the database used to extract the reference descriptor. Alternatively, in the example in which the BodyGPS method comprises determining the feature that is closest to the initial set of coordinates 700, the identified feature may be used to identify the reference location and reference descriptor.

Figure 11:
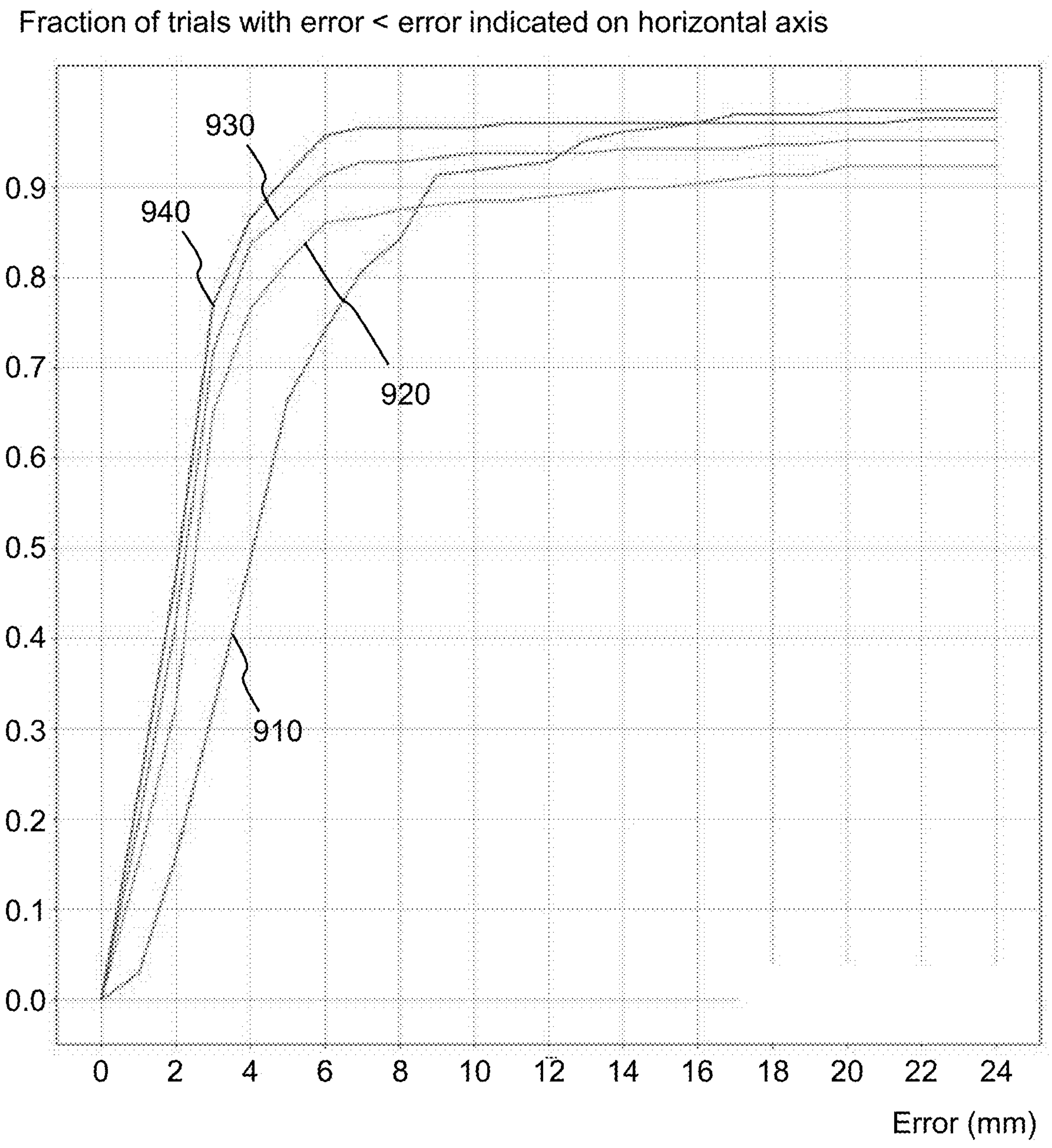
FIG. 11 is a graph illustrating the performance of several methods for determining a location at which a given feature is represented in target medical imaging data.

In some examples, the one or more sets of reference medical imaging data 220 comprises a plurality of sets of reference medical imaging data 220. In these examples, the reference location is, for each of the one or more sets of reference medical imaging data 220, a location in the set of reference medical imaging data 220 at which the given feature 226 is represented, and the reference descriptor is an averaged reference descriptor obtained from the plurality of sets of reference medical imaging data 220. The inventors have realized that using an averaged reference descriptor obtained from a plurality of sets of reference medical imaging data 220 can improve the accuracy of the determined location at which the given feature 226 is represented. The results of this are illustrated in FIG. 11.

The plurality of sets of reference medical imaging data 220 may be sets of reference medical imaging data 220 that represent different patients. This can help to mitigate the effect of anatomical deviations of a patient in one set of reference medical imaging data 220 from typical body metrics in a single set of medical imaging data, on the comparison of step 128. Alternatively, the plurality of sets of medical imaging data may be sets of reference medical imaging data 220 that relate to the same patient. This can help to mitigate against the effect of noise in the reference medical imaging data 220 on the comparison. In any case, the plurality of sets of reference medical imaging data 220 may include the given feature 226. An image registration process may be performed to transform the plurality of sets of reference medical imaging data 220 to a single coordinate system. This would reduce the effects of e.g. slightly different orientations of the sets of medical imaging data.

In one example, the averaged reference descriptor is an average of a plurality of reference descriptors. Each of the plurality of reference descriptors is a reference descriptor for the reference location in a respective one of the plurality of sets of reference medical imaging data 220. Each of the plurality of reference descriptors is representative of values of elements of the respective set of reference medical imaging data 220 located relative to the reference location according to the second predefined pattern 440.

In another example, the averaged reference descriptor is a reference descriptor for an "average image" of the plurality of sets of medical imaging data. For example, the plurality of sets of medical imaging data may represent, for each of a plurality of element (e.g. pixel/voxel) locations, a value, such as an intensity value. An image registration process may be performed on the plurality of sets of medical imaging data so that each set of medical imaging data is represented in the same coordinate system. For each element location of the registered sets of medical imaging data, the values of the different sets may be averaged to obtain an average value. The "average image" is an image that comprises the average values for each element location.

As mentioned, the method comprises, in step 128, for each of the plurality of candidate locations 442, comparing the reference descriptor and the candidate descriptor for the candidate location to obtain a similarity metric.

In some examples, the similarity metric may comprise the normalized mutual information similarity between the reference descriptor and the candidate descriptor. In some examples, other similarity metrics between the first descriptor and the second descriptor may be used. For example, cosine similarity, Euclidean distance, and/or cross correlation may alternatively or additionally be used.

As mentioned, the method comprises, in step 130, selecting a candidate location from among the plurality of candidate locations 442 based on the calculated similarity metrics; and in step 132, determining the location at which the given feature 226 is represented in the target medical imaging data 330 based on the selected candidate location.

In some examples, selecting the candidate location may comprise selecting the candidate location having the similarity metric indicating the highest degree of similarity among the similarity metrics of the plurality of candidate locations 442, 340. For example, the candidate location with the highest mutual information similarity metric may be selected. In some examples, determining the location at which the given feature 226 is represented comprises determining, as the location at which the given feature 226 is represented in the target medical imaging data 330, the selected candidate location. In the example shown in FIG. 9, the approximate location used to determine the candidate locations is the candidate location that has the highest similarity metric, and is hence selected as the selected candidate location.

In some examples, the selected candidate location 448 may be taken as the location at which the given feature 226 is represented in the target medical imaging data 330. However, in other examples, this determined location may be refined by defining further candidate locations 444 (based on the selected candidate location 448) in successively more fine-grained patterns (see e.g. the pattern of black circles 444 in FIG. 9). Accordingly, an accurate yet efficient determination of the location at which a given feature 226 is represented in the target medical imaging data 330 may be provided for.

Specifically, in these examples, the method comprises determining, based on the determined location at which the given feature 226 is represented in the target medical imaging data 330, a plurality of further candidate locations 444 in the target medical imaging data 330. For example, the further candidate locations may be defined as locations in the region of the selected candidate location. For example, the further candidate locations may be defined as locations in the region of (i.e. local to) the selected candidate location 448. For example, the candidate locations may be arranged in a square 3×3 grid centered on the approximate location, and the further candidate locations may be arranged in a smaller square 3×3 grid based on the previously determined location at which the given feature 226 is represented.

The method may then comprise obtaining a further candidate descriptor for each of the plurality of further candidate locations 444 in the target medical imaging data 330, each further candidate descriptor being representative of values of elements of the second medical imaging data 330 located relative to the respective further candidate location 444 according to the second predefined pattern 440. For example, the further candidate descriptor may be the same as, i.e. may have been calculated in the same way as, the reference and candidate descriptors as described above.

The method may then comprise, for each of the plurality of further candidate locations 444, comparing the reference descriptor and the further candidate descriptor for the candidate location to obtain a further similarity metric. For example, the further similarity metric may be the same as, i.e. may be calculated in the same way as, the similarity metric as used between the reference descriptor and the candidate descriptors. The method may then comprise selecting a further candidate location from among the plurality of further candidate locations 444 based on the further similarity metrics. For example, as illustrated in FIG. 9, the further candidate location 446 with the highest similarity metric may be selected. The method may then comprise determining the location at which the given feature 226 is represented in the target medical imaging data 330 based on the selected further candidate location 446.

In some examples, the selected further candidate location 446 may be taken as the location at which the given feature 226 is represented in the target medical imaging data 330. However, in other examples, this determined location may be further refined by defining yet further candidate locations based on the selected further candidate location 446, and repeating the above-described method for these yet further candidate locations.

In any case, the location at which the given feature 226 is represented in the target medical imaging data 330 is determined. In some examples, the method may further comprise generating output data indicating the determined location at which the given feature 226 is represented in the target medical imaging data 330.

Figure 10:
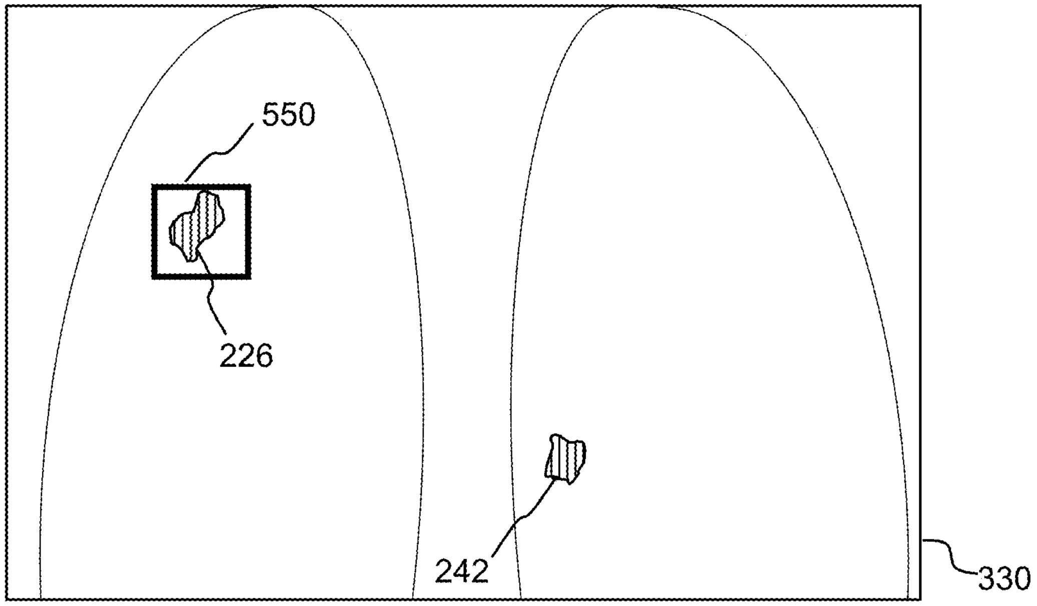
FIG. 10 is a diagram illustrating schematically target medical imaging data according to another example.

For example, the output data may comprise a coordinate or pixel/voxel index corresponding to the determined location, 446 within the target medical imaging data 330. In some examples, the output data may further comprise a reference to the target medical imaging data 330 within which the location has been determined. In some examples, the output data may comprise the target medical imaging data 330 itself (or a portion thereof). In some examples, the output data may comprise an image (or data for an image) in which an indicator indicating the determined location is overlaid onto a rendering of the target medical imaging data 330. For example, as illustrated in FIG. 10, a representation of the target medical imaging data 330 is shown, and overlaid onto (or otherwise included in) the representation is an indicator 550 indicating the location at which the given feature 226 is represented in the target medical imaging data 330. In this example, the indicator is a box centered on the determined location. However in other examples other indicators may be used, such as a marker or dot or other symbol overlaid (or otherwise included) at the determined location; or for example an arrow or pointer or other label pointing at or connected or otherwise indicating the determined location. The output data may allow for an indication to be provided to a user, e.g. a physician, as to the determined location at which the given feature 226 is represented in the target medical imaging data 330. In some examples, the output data may be stored in a storage device. For example, the output data may be stored in a database. This may allow for the output data to be referred to, for example by a user or by an automated downstream process (not shown).

In some examples, the method may comprise transmitting the output data to a display device to display a representation of the target medical imaging data 330 and an indicator 550 indicating, on the representation of the target medical image data, the determined location at which the given feature 226 is represented. For example, the display device (not shown) may be a computer monitor or other display screen of a computer. For example, the displayed representation may be similar to that shown in FIG. 10, where the indicator 550 is overlaid onto the representation of the second medical imaging data 330. Any of the example indicators mentioned above may be used. This may allow for a user, e.g. a physician, to immediately and easily appreciate the location at which the given feature 226 is represented in the target medical imaging data 330, which may, for example, allow for assessments based on the given feature 226 to be made more quickly and with minimal burden.

In some examples, the method comprises performing an image registration process using the location at which the given feature 226 is represented in the target medical imaging data 330. For example, the location at which the given feature 226 is represented may be used as one of a set of transformations of the target medical imaging data 330 to a coordinate system. For example, the target medical imaging data 330 may be registered with a reference medical image showing the given feature 226, such as the reference medical imaging data 220, using the location at which the given feature 226 is represented in the target medical imaging data 330 and the location in the reference medical image at which the given feature 226 is represented.

The above-described registration process can be made as accurate as desired, by adjusting the number of iterations used in the hierarchical point matching method 120 to determine the location at which the given feature 226 is represented. If computational efficiency is desired, the number of iterations can be reduced, while if greater image registration accuracy is desired, the number of iterations can be raised.

In some examples, the method comprises performing steps 112 to 132 to determine a location at which a further feature is represented in the target medical imaging data 330. For example, a further feature in the above-described database providing correspondences between features and locations of the features in the reference medical imaging data 220, may be used as a basis to perform steps 112 to 132 to determine the location at which the further feature is represented in the target medical imaging data 330. A plurality of locations of features in the target medical imaging data 330 may be determined in this way. The registration process may comprise using the location at which the further feature is represented in the target medical imaging data 330. This may improve the accuracy of the image registration process.

Using the hierarchical method described above may allow for the location to be accurately determined.

It is possible to determine the location using a point matching method without using BodyGPS to firstly identify the approximate location. For instance, instead of determining the candidate locations based on the approximate location, the candidate locations could initially be spread in a uniform coarse grid across the entire target medical image. Iterations of the point matching method 120 could be applied to gradually narrow down the area of the grid that could contain the given feature 226, specifically by using the selected candidate location determined at one iteration of the point matching method 120 to determine further candidate locations for the next iteration. After a certain number of iterations, the selected candidate location can be identified as a location at which the given feature 226 is represented.

However, testing the entire target medical imaging data 330 in this undirected way would require performing a large number iterations of the point matching method 120 to accurately determine the location. At each iteration, many comparisons between the candidate descriptors for that iteration and the reference descriptor would be required. This is computationally expensive. Furthermore, as discussed previously, since such a method would involve determining the location in the image whose descriptor has the highest similarity with the reference descriptor, the method may produce a false positive indication of the location at which the given feature 226 is represented-a location where the given feature 226 is not actually represented, but is nevertheless the location in the target medical imaging data 330 whose descriptor is most similar to the reference descriptor.

The present framework addresses the above problems by using the BodyGPS method 110 to provide an approximate location, on the basis of which the candidate locations are determined. Since the BodyGPS method 110 can determine whether the given feature is represented in the target medical imaging data 330, the risk of a false positive indication of the location of the given feature 226 is reduced, compared with using the point matching method 120 alone. Furthermore, since the BodyGPS method 110 provides the approximate location of the landmark on which the point matching method 120 is initiated, the area or volume of target medical imaging data over which the point matching method 120 is applied can be significantly reduced. In other words, the number of iterations of the point matching method 120 needed to achieve a particular level of accuracy for the location, can be reduced significantly by firstly using the BodyGPS method 110 to determine the approximate location. Hence, the present framework may be more computationally efficient than using the point matching method 120 alone.

In addition, while the BodyGPS method 110 can be applied alone to determine an approximate location at which the given feature 226 is represented, this accuracy and/or precision of this approximate location may be limited, for example due to the limited granularity of body locations on the basis of which the machine learning model was trained. However, the point matching method 120 involves directly comparing descriptors of candidate locations determined from the approximate location with reference descriptors. This can be performed with arbitrary granularity (for example down to the individual pixel level), which can improve the accuracy and/or precision of the determined location.

FIG. 11 illustrates a graph showing the accuracy of each of several methods for determining the location at which the tracheal carina is represented in medical imaging data. The horizontal axis indicates the error on the determined location, measured as the distance in millimeters between the determined location and the true location of the tracheal carina. The vertical axis indicates the fraction of tested sets of medical imaging data for which the error is less than the error indicated on the horizontal axis.

Curve 910 indicates the accuracy of the approximate location produced by the BodyGPS method 110, where the BodyGPS method 110 uses 24 iterations of the refining process (in other words, 25 iterations of the BodyGPS method in total). As can be seen in the Figure, the approximate location determined by the BodyGPS method 110 is correct to 6 mm for approximately 74% of tested sets of medical imaging data. Curve 920 indicates the accuracy of the location obtained by using four iterations of the hierarchical point matching method 120 alone. The location determined using this method is correct to 6 mm for approximately 86% of tested sets of medical imaging data.

Curve 930 indicates the accuracy of the location obtained by using the BodyGPS method 110 and 24 iterations of the refining process (in other words, 25 iterations of the Body GPS method in total) to determine the approximate location and then using one iteration of the point matching method 120 to refine this location, where the reference descriptor used for the point matching method 120 is obtained from a single set of medical imaging data. The location determined using this method is correct to 6 mm for approximately 91% of tested sets of medical imaging data. This experiment thus demonstrates that the combination of the BodyGPS method 110 with the point matching method 120 produces a method that is more accurate than either the BodyGPS method 110 or one iteration of the point matching method 120 alone.

Curve 940 indicates the accuracy of the location obtained by using the BodyGPS method 110 to determine the approximate location and then using the point matching method 120 to refine this location (as per curve 930), but where the reference descriptor used for the point matching method 120 is obtained by averaging descriptors from a plurality of sets of medical imaging data in the fashion described above. The location determined using this method is correct to 6 mm for approximately 96% of tested sets of medical imaging data. This experiment thus demonstrates that using an averaged reference descriptor obtained from a plurality of sets of medical imaging data produces a method that is more accurate than one which uses a reference descriptor obtained from a single set of medical imaging data.

Described hereinafter is an example method that may be used to train the trained machine learning model 715 used in the BodyGPS method 110.

The training method comprises providing a machine learning model configured to generate, based on an input of data representative of a given descriptor, a set of coordinates representing a body location in the template body 705. The given descriptor is representative of values of elements of given medical imaging data located relative to a given location in the given medical imaging data according to a first predefined pattern.

The machine learning model may comprise, for example, a convolutional neural network. The machine learning model may perform a dimension reduction operation, such as an average pooling operation, on any medical imaging data input to it. The dimension-reduced medical imaging data may be processed using a plurality of layers of the convolutional neural network. The convolutional neural network may be configured to output the set of coordinates. The convolutional neural network may be configured to apply a sigmoid function to a set of coordinates that has been obtained by processing the dimension-reduced medical imaging data using the plurality of layers, to output a set of coordinates which each have a reduced range, such as 0 to 1.

The training method comprises providing training data comprising a plurality of training descriptors. Each training descriptor is representative of values of elements of a given set of medical imaging data located relative to a given location in a given set of medical imaging data according to the first predefined pattern. The training data further comprises, for each training descriptor, a ground truth set of coordinates associated with a respective body location in the template body 705.

The training descriptors may be obtained from respective sets of training medical imaging data. The training descriptors may be obtained using the same descriptor model that is used to obtain the initial descriptor, the reference descriptor, and the candidate descriptors.

In some examples, the point matching method 120 can be used to determine the training descriptor. In these examples, providing the training data comprises obtaining one of the plurality of training descriptors by firstly obtaining a template descriptor for a reference location in template medical imaging data. The template medical imaging data may be identical to the reference medical imaging data 220 used in the point matching method 120. The reference location is a location in the template medical imaging data at which the respective body location is represented. Here, the respective body location is the body location associated with the ground truth set of coordinates. The template descriptor is representative of values of elements of the template medical imaging data located relative to the reference location according to the second predefined pattern 440. The template descriptor may be obtained using the same descriptor model that is used to obtain the initial descriptor, the reference descriptor, and the candidate descriptors.

In these examples, obtaining the training descriptor comprises obtaining candidate descriptors for each of a plurality of candidate locations 442 in the given set of medical imaging data. Each candidate descriptor is representative of values of elements of the given set of medical imaging data located relative to the candidate location according to the second predefined pattern 440. The candidate descriptors referred to here may be obtained using the same descriptor model that is used to obtain the initial descriptor and the reference descriptors, and in a similar fashion to that described above with reference to step 124. The candidate locations may be located in a predefined pattern throughout the given set of medical imaging data; for example, the candidate locations may be located as the nodes of a square 3×3 grid covering the given set of medical imaging data.

In these examples, obtaining the training descriptor comprises, for each of the plurality of candidate locations 442 in the given set of medical imaging data, comparing the template descriptor and the candidate descriptor for the candidate location to obtain a template similarity metric. This may be performed in a similar fashion to that described above with reference to step 128.

In these examples, obtaining the training descriptor comprises determining the training descriptor based on the candidate descriptors and the calculated template similarity metrics. For example, the candidate descriptor having the highest similarity metric with the template descriptor may be selected as the training descriptor.

The candidate location of the selected candidate descriptor may be used to determine further candidate locations near the selected candidate location to find a further candidate descriptor with an even higher similarity to the template descriptor, as described above in the hierarchical point matching method 120.

The training method may comprise determining the ground truth set of coordinates based on the reference location in the template medical imaging data. For example, where the template medical imaging data (which may be identical to the reference medical imaging data 220) is a panoramic image, the ground truth set of coordinates may be determined as the reference location in the panoramic image.

The above method to obtain the training descriptors may be used to obtain all of the training descriptors. Respective reference locations in the template medical imaging data may be used as a basis for performing the point matching method 120 to obtain the training descriptor from a given set of medical imaging data. In some examples, for each set of ground truth coordinates, a plurality of training descriptors may be obtained from a respective plurality of medical images.

The training method comprises training the machine learning model based on the training data so as to minimize a loss function between sets of coordinates generated by the machine learning model based on the training descriptors, and the corresponding ground truth sets of coordinates. The loss function may comprise, for example, a function that measures the Euclidean distance, or the cosine distance, between the sets of coordinates generated by the machine learning model based on the training descriptors, and the corresponding ground truth sets of coordinates. The loss function may be any increasing function of one of these distances.

Thus, the machine learning model can be trained to generate, based on an input of data representative of a given descriptor, a set of coordinates representing a body location in the template body 705.

This method of training the machine learning model does not require any supervision. Instead of manually annotating the location in a set of training medical imaging data at which a given feature 226 (e.g. landmark) is represented, and obtaining a training descriptor for this landmark, the point matching method 120 is used to automatically determine the training descriptors for the ground truth sets of coordinates. This training method thus improves the efficiency of the training of a machine learning model for determining an approximate location at which a given feature 226 (e.g. landmark) is represented in medical imaging data.

In examples where the trained machine learning model 715 outputs directly the vector 720 between the initial set of coordinates 700 and the set of feature coordinates 730 in step 114, the training process may be modified by providing, instead of the ground truth sets of coordinates, a ground truth vector between the set of coordinates associated with the body location represented by the reference location, and the desired body location. For example, an arbitrary vector can be subtracted from the ground truth set of coordinates determined using the above-described method to obtain an offset location, and a descriptor can be obtained for the offset location. The training process would comprise training the machine learning model so as to minimize a loss function between vectors generated by the machine learning model based on the descriptors for the offset locations, and the corresponding ground truth vectors.

Figure 12:
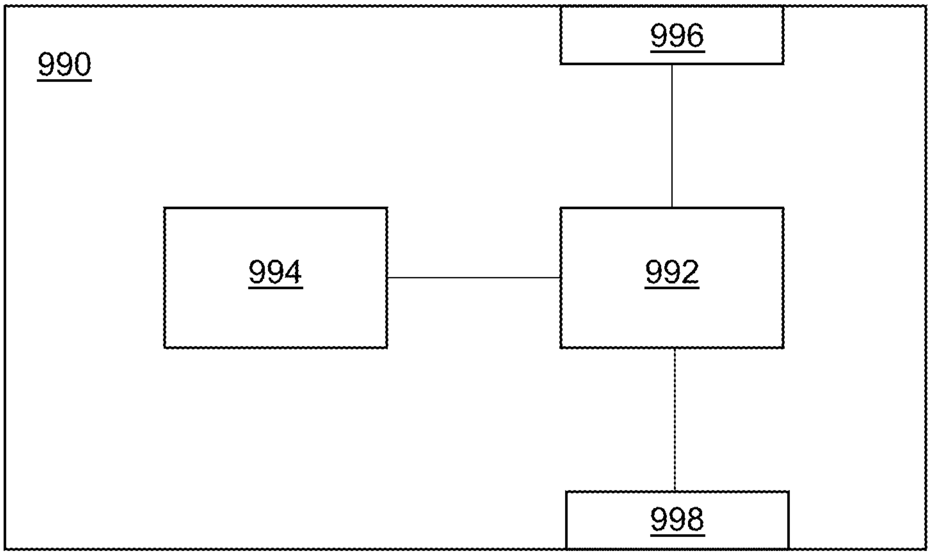
FIG. 12 is a diagram illustrating an apparatus according to an example.

Referring to FIG. 12, there is illustrated an apparatus 990 according to an example. The apparatus 990 comprises an input interface 996, an output interface 998, a processor 992, and a non-transitory memory device 994. The processor 992 and the memory device 994 may be configured to perform the method according to any one of the examples described above with reference to FIGS. 1 to 10. The memory device may store computer readable program code or instructions which, when executed by the processor 992 case the processor 992 to perform the method according to any one of the examples described above with reference to FIGS. 1 to 10. The instructions may be stored on any one or more computer readable media, for example any one or more non-transitory computer readable media.

For example, the input interface 996 may receive the target medical imaging data 330 and data representing the given feature 226. The processor 992 may implement the method according to any of the examples described above with reference to FIGS. 1 to 9, and the processor 992 may output, via the output interface 998, data indicating the determined location at which the given feature 226 is represented in the second medical imaging data 330, for example the output data as described above with reference to FIG. 10. In some examples, the output data may be transmitted to a storage (not shown) for example implementing a database, so that the output data is stored in the storage. In some examples, the output data may be transmitted to a display device (not shown) to allow a user to review the output data, for example as described above with reference to FIG. 10. In some examples, the output data may be stored, alternatively or additionally, in the memory 994.

The apparatus 990 may be implemented as a processing system and/or a computer. It will be appreciated that the methods according to any one of the examples described above with reference to FIGS. 1 to 10 are computer implemented methods, and that these methods may be implemented by the apparatus 990.

The above examples are to be understood as illustrative examples of the invention. It is to be understood that any feature described in relation to any one example may be used alone, or in combination with other features described, and may also be used in combination with one or more features of any other of the examples, or any combination of any other of the examples. Furthermore, equivalents and modifications not described above may also be employed without departing from the scope of the invention, which is defined in the accompanying claims.

What is claimed is:

1. A computer implemented method of determining a location at which a given feature is represented in target medical imaging data, the target medical imaging data comprising an array of elements having respective values and representing respective locations, the method comprising:

- obtaining an initial descriptor for an initial location in the target medical imaging data, the initial descriptor being representative of values of elements of the target medical imaging data located relative to the initial location according to a first predefined pattern;
- determining, based on an input of data representative of the initial descriptor to a trained machine learning model, an approximate location in the target medical imaging data at which the given feature is represented;
- determining, based on the approximate location, a plurality of candidate locations in the target medical imaging data;
- obtaining candidate descriptors for each of the plurality of candidate locations, each candidate descriptor being representative of values of elements of the target medical imaging data located relative to the candidate location according to a second predefined pattern;
- obtaining a reference descriptor for a reference location in reference medical imaging data, the reference medical imaging data comprising one or more sets of reference medical imaging data, the reference location being, for each of the one or more sets of reference medical imaging data, a location in the set of reference medical imaging data at which the given feature is represented, the reference descriptor being representative of, for each of the one or more sets of reference medical imaging data, values of elements of the set of reference medical imaging data located relative to the reference location according to the second predefined pattern;
- for each of the plurality of candidate locations, comparing the reference descriptor and the candidate descriptor for the candidate location to obtain a similarity metric;
- selecting a candidate location from among the plurality of candidate locations based on the similarity metrics; and
- determining the location at which the given feature is represented in the target medical imaging data based on the selected candidate location.

2. The computer implemented method of claim 1, further comprising:

- determining, based on the determined location at which the given feature is represented in the target medical imaging data, a plurality of further candidate locations in the target medical imaging data, wherein a distance between the further candidate locations is less than a distance between the candidate locations;
- obtaining further candidate descriptors for each of the plurality of further candidate locations, each further candidate descriptor being representative of values of elements of the target medical imaging data located relative to the further candidate location according to the second predefined pattern;
- for each of the plurality of further candidate locations, comparing the reference descriptor and the further candidate descriptor for the candidate location to obtain a further similarity metric;
- selecting a further candidate location from among the plurality of further candidate locations based on the further similarity metrics; and
- determining a refined location at which the given feature is represented in the target medical imaging data based on the selected further candidate location.

3. The computer implemented method of claim 1, further comprising:

- performing an image registration process using the location at which the given feature is represented in the target medical imaging data.

4. The computer implemented method of claim 3, further comprising:

- determining a location at which a further feature is represented in the target medical imaging data, wherein performing the image registration process comprises performing the image registration process using the location at which the further feature is represented in the target medical imaging data.

5. The computer implemented method of claim 1, wherein determining the location at which the given feature is represented comprises determining, as the location at which the given feature is represented in the target medical imaging data, the selected candidate location.

6. The computer implemented method of claim 1, wherein the one or more sets of reference medical imaging data comprises a plurality of sets of reference medical imaging data, and the reference descriptor is an averaged reference descriptor obtained from the plurality of sets of reference medical imaging data.

7. The computer implemented method of claim 1, wherein determining the approximate location comprises:

- generating, based on an input of data representative of the initial descriptor to the trained machine learning model, an initial set of coordinates representing an initial body location in a template body, the initial body location in the template body corresponding to a body location, in a body at least a portion of which is represented by the target medical imaging data, represented at the initial location in the target medical imaging data; and based on the initial set of coordinates, a set of feature coordinates representing a location of the given feature in the template body, and the initial location, determining the approximate location.

8. The computer implemented method of claim 7, wherein determining the approximate location comprises calculating a vector between the initial set of coordinates and the set of feature coordinates, and calculating the approximate location based on the initial location and the vector.

9. The computer implemented method of claim 8, wherein calculating the approximate location comprises adding the vector to a vector representation of the initial location.

10. The computer implemented method of claim 7, further comprising performing a refining process to refine the approximate location.

11. The computer implemented method of claim 10, wherein the refining process comprises:

determining, based on the initial set of coordinates and the set of feature coordinates, a direction;

determining, based on the initial location and the direction, a further initial location in the target medical imaging data;

obtaining a further descriptor for the further initial location, the further descriptor being representative of values of elements of the target medical imaging data located relative to the further initial location according to the first predefined pattern;

generating, based on the input of the data representative of the further descriptor to the trained machine learning model, a further initial set of coordinates representing a further initial body location in the template body, the further initial body location in the template body corresponding to a body location, in the body at least a portion of which is represented by given medical imaging data, represented at the further initial location in the target medical imaging data; and based on the further initial set of coordinates, the set of feature coordinates representing the location of the given feature in the template body, and the further initial location, determining the approximate location.

12. The computer implemented method of claim 11, wherein determining the direction comprises determining, as the direction, a direction of a vector between the initial set of coordinates and the set of feature coordinates.

13. The computer implemented method of claim 7, wherein the trained machine learning model has been trained by a training method comprising:

providing a machine learning model configured to generate, based on an input of data representative of a given descriptor, a set of coordinates representing a body location in the template body, the given descriptor being representative of values of elements of given medical imaging data located relative to a given location in the given medical imaging data according to the first predefined pattern;

providing training data comprising a plurality of training descriptors, each training descriptor being representative of values of elements of a given set of medical imaging data located relative to a given location in the given set of medical imaging data according to the first predefined pattern, the training data further comprising, for each training descriptor, a ground truth set of coordinates associated with a respective body location in the template body; and training the machine learning model based on the training data so as to minimize a loss function between sets of coordinates generated by the machine learning model based on the training descriptors and the corresponding ground truth sets of coordinates.

14. The computer implemented method of claim 13, wherein providing the training data comprises obtaining one of the plurality of training descriptors by:

obtaining a template descriptor for a reference location in template medical imaging data, the reference location in the template medical imaging data being a location in the template medical imaging data at which the respective body location is represented, the template descriptor being representative of values of elements of the template medical imaging data located relative to the reference location according to the second predefined pattern;

obtaining candidate descriptors for each of a plurality of candidate locations in the given set of medical imaging data, each candidate descriptor being representative of values of elements of the given set of medical imaging data located relative to the candidate location according to the second predefined pattern;

for each of the plurality of candidate locations in the given set of medical imaging data, comparing the template descriptor and the candidate descriptor for the candidate location to obtain a template similarity metric; and determining the training descriptor based on the candidate descriptors and the template similarity metrics.

15. An apparatus for determining a location at which a given feature is represented in target medical imaging data, the target medical imaging data comprising an array of elements having respective values and representing respective locations, comprising:

a non-transitory memory device for storing computer readable program code; and a processor in communication with the non-transitory memory device, the processor being operative with the computer readable program code to perform steps including obtaining an initial descriptor for an initial location in the target medical imaging data, the initial descriptor being representative of values of elements of the target medical imaging data located relative to the initial location according to a first predefined pattern, determining, based on an input of data representative of the initial descriptor to a trained machine learning model, an approximate location in the target medical imaging data at which the given feature is represented, determining, based on the approximate location, a plurality of candidate locations in the target medical imaging data, obtaining candidate descriptors for each of the plurality of candidate locations, each candidate descriptor being representative of values of elements of the target medical imaging data located relative to the candidate location according to a second predefined pattern, obtaining a reference descriptor for a reference location in reference medical imaging data, the reference medical imaging data comprising one or more sets of reference medical imaging data, the reference location being, for each of the one or more sets of reference medical imaging data, a location in the set of reference medical imaging data at which the given feature is represented, the reference descriptor being representative of, for each of the one or more sets of reference medical imaging data, values of elements of the set of reference medical imaging data located relative to the reference location according to the second predefined pattern, for each of the plurality of candidate locations, comparing the reference descriptor and the candidate descriptor for the candidate location to obtain a similarity metric, selecting a candidate location from among the plurality of candidate locations based on the similarity metrics, and determining the location at which the given feature is represented in the target medical imaging data based on the selected candidate location.

16. The apparatus of claim 15, wherein the processor is operative with the computer readable program code to perform further steps comprising:

determining, based on the determined location at which the given feature is represented in the target medical imaging data, a plurality of further candidate locations in the target medical imaging data, wherein a distance between the further candidate locations is less than a distance between the candidate locations;

obtaining further candidate descriptors for each of the plurality of further candidate locations, each further candidate descriptor being representative of values of elements of the target medical imaging data located relative to the further candidate location according to the second predefined pattern;

for each of the plurality of further candidate locations, comparing the reference descriptor and the further candidate descriptor for the candidate location to obtain a further similarity metric;

selecting a further candidate location from among the plurality of further candidate locations based on the further similarity metrics; and determining a refined location at which the given feature is represented in the target medical imaging data based on the selected further candidate location.

17. The apparatus of claim 15, wherein determining the location at which the given feature is represented comprises determining, as the location at which the given feature is represented in the target medical imaging data, the selected candidate location.

18. The apparatus of claim 15, wherein the one or more sets of reference medical imaging data comprises a plurality of sets of reference medical imaging data, and the reference descriptor is an averaged reference descriptor obtained from the plurality of sets of reference medical imaging data.

19. The apparatus of claim 15, wherein determining the approximate location comprises:

generating, based on an input of data representative of the initial descriptor to the trained machine learning model, an initial set of coordinates representing an initial body location in a template body, the initial body location in the template body corresponding to a body location, in a body at least a portion of which is represented by the target medical imaging data, represented at the initial location in the target medical imaging data; and based on the initial set of coordinates, a set of feature coordinates representing a location of the given feature in the template body, and the initial location, determining the approximate location.

20. One or more non-transitory computer-readable media embodying instructions executable by machine to perform operations for determining a location at which a given feature is represented in target medical imaging data, the target medical imaging data comprising an array of elements having respective values and representing respective locations, the operations comprising:

obtaining an initial descriptor for an initial location in the target medical imaging data, the initial descriptor being representative of values of elements of the target medical imaging data located relative to the initial location according to a first predefined pattern;

determining, based on an input of data representative of the initial descriptor to a trained machine learning model, an approximate location in the target medical imaging data at which the given feature is represented;

determining, based on the approximate location, a plurality of candidate locations in the target medical imaging data;

obtaining candidate descriptors for each of the plurality of candidate locations, each candidate descriptor being representative of values of elements of the target medical imaging data located relative to the candidate location according to a second predefined pattern;

obtaining a reference descriptor for a reference location in reference medical imaging data, the reference medical imaging data comprising one or more sets of reference medical imaging data, the reference location being, for each of the one or more sets of reference medical imaging data, a location in the set of reference medical imaging data at which the given feature is represented, the reference descriptor being representative of, for each of the one or more sets of reference medical imaging data, values of elements of the set of reference medical imaging data located relative to the reference location according to the second predefined pattern;

for each of the plurality of candidate locations, comparing the reference descriptor and the candidate descriptor for the candidate location to obtain a similarity metric;

selecting a candidate location from among the plurality of candidate locations based on the similarity metrics; and determining the location at which the given feature is represented in the target medical imaging data based on the selected candidate location.

* * * * *